United States Patent
Michelsson

(10) Patent No.: US 7,193,699 B2
(45) Date of Patent: Mar. 20, 2007

(54) METHOD AND APPARATUS FOR SCANNING A SEMICONDUCTOR WAFER

(75) Inventor: Detlef Michelsson, Wetzlar-Naunheim (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 271 days.

(21) Appl. No.: 10/774,520

(22) Filed: Feb. 9, 2004

(65) Prior Publication Data

US 2005/0002022 A1 Jan. 6, 2005

(30) Foreign Application Priority Data

Feb. 21, 2003 (DE) ................................ 103 07 358

(51) Int. Cl.
*G01N 21/00* (2006.01)
(52) U.S. Cl. ................................ 356/237.5; 356/237.2
(58) Field of Classification Search ...................... None
See application file for complete search history.

(56) References Cited

U.S. PATENT DOCUMENTS

| 6,650,409 | B1 * | 11/2003 | Noguchi et al. | ......... 356/237.3 |
| 2003/0092267 | A1 * | 5/2003 | Kian et al. | ................... 438/690 |
| 2005/0214956 | A1 * | 9/2005 | Li et al. | ....................... 438/14 |
| 2005/0232362 | A1 * | 10/2005 | Lee | ........................ 375/240.23 |
| 2005/0253093 | A1 * | 11/2005 | Gorski et al. | .......... 250/492.22 |
| 2005/0254698 | A1 * | 11/2005 | Young et al. | ............... 382/145 |

* cited by examiner

*Primary Examiner*—Michael P. Stafira
(74) *Attorney, Agent, or Firm*—Houston Eliseeva LLP

(57) ABSTRACT

The invention is based on a method and an apparatus for scanning a semiconductor wafer (1), on-the-fly images of regions on the wafer being acquired using a camera (3). Upon a scan line changeover, a continuously curved displacement track is generated by at least partial superimposition of the relative motions between the wafer (1) and camera (3) in the direction of the scan lines and perpendicular thereto. As a result, time is saved and wafer throughput is increased.

17 Claims, 3 Drawing Sheets

METHOD AND APPARATUS FOR SCANNING A SEMICONDUCTOR WAFER

RELATED APPLICATIONS

This application claims priority of the German patent application 103 07 358.2 which is incorporated by reference herein.

FIELD OF THE INVENTION

The invention is based on a method and an apparatus for scanning a semiconductor wafer, in which the wafer is scanned in scan lines, and images of regions on the wafer are acquired with a camera at a scanning speed in the scan line direction as a relative motion between the camera and the wafer.

BACKGROUND OF THE INVENTION

In the manufacture of integrated circuits, features are applied onto semiconductor wafers. A plurality of process steps are required for this, and various defects can occur on the wafer in that context. Defects can form in the features and substrate materials, or particles can settle onto the wafer surface. In order to detect these defects, the wafers are often examined macroscopically or even microscopically after each process step. These inspections are performed, in the context of the usually automated systems, by means of a camera that acquires images of the regions to be examined on the wafer. The images are evaluated by means of image processing in order to detect and classify defects.

In addition, features applied onto the wafers can also be measured. In this context, the feature spacings and feature widths are determined in order to ascertain deviations from target values. An offset of features with respect to features resulting from the previous process can also be identified. Such defects can once again be ascertained by way of an image processing system.

In the case of layers that are applied onto the wafer, it is likewise possible to identify, by way of the image processing system, color changes that are attributable to coating defects such as inhomogeneous layer thicknesses or regions where layers are absent.

The wafers to be inspected are usually placed on a scanning stage. The scanning stage is displaced beneath a camera or also beneath a macroscope or microscope fitted with a camera. Depending on the type of manufacturing process, regions on the wafer intended for subsequent inspection are selected and moved to with the scanning stage, and images thereof are acquired with the camera.

Because the features being manufactured are becoming increasingly small and more susceptible to defects, and as a result of higher manufacturing costs for larger-diameter wafers, 100% inspection of the wafer after the respective process steps is more often being demanded. This naturally requires a greater expenditure of time than for random inspection of a few individual regions on the wafer surface. Nevertheless, a greater throughput of wafers for inspection must also be guaranteed.

For these reasons, the images of the wafer surface are acquired "on the fly." This normally involves moving a scanning stage, on which the wafer is placed, beneath a stationary camera. The scanning stage does not stop for an image acquisition but instead displaces the wafer through beneath the camera, generally at a constant speed. The camera acquires the images using a correspondingly short exposure time. This is often achieved by illuminating the region of the wafer located in the camera's image field with a short, high-intensity flash of light. The camera's electronic chip is exposed during this short time interval, and acquires an image of that region of the wafer.

When scanning a wafer, it is usual to orient the camera's rectangular image field so that the longer side of the image field rectangle is parallel to the scan lines. The longer side of the rectangle thus points in the direction of motion of the scanning stage.

The scanning stage is furthermore scanned in a rectangular, meander-shaped fashion in order to shorten the throughput time for wafer inspection. The displacement track thus contains, at the changeover to a scanning line to be scanned next, portions at right angles to one another.

The scanning stage is displaced over a predefined path in each scan line. The path is longer than the wafer diameter so that the wafer can be completely covered. At the end of each scan line the scanning stage is stopped and then moved to the adjacent scan line in the direction perpendicular to the scan line, and the scanning operation is then continued in the opposite direction in the new scan line. The displacement paths at the scan line changeover are thus at right angles to one another, and the displacement track is rectangular in shape. This process repeats at each scan line changeover.

SUMMARY OF THE INVENTION

It is the object of the invention to describe a method and an apparatus with which the throughput time upon scanning a semiconductor for wafer inspection can be further optimized.

The object is achieved, with a method for scanning a semiconductor wafer, comprising the steps of:
scanning the wafer with a plurality of scan lines by creating a relative motion between a camera and the wafer,
acquiring images of regions on the wafer with the camera at a scanning speed in a direction of one scan line,
changing from a current scan line to a new scan line that is to be scanned next, by:
   providing a deceleration of the relative motion in the scan line direction in the scan line until that relative motion comes to a standstill, and
   providing acceleration in the opposite scan line direction until the scanning speed is reached, and
superimposing at least partially the acceleration and subsequent deceleration of a relative motion between the camera and wafer the until the new scan line is reached.

The object is moreover achieved, with an apparatus comprising: a camera for on-the-fly acquisition of images of a plurality of regions on the wafer, means for generating a relative motion between the camera and the wafer thereby defining a scanning speed in a direction of the scan line, a control device with which, upon a changeover from a current scan line to a new scan line that is to be scanned next, a deceleration of the relative motion in the direction of the scan line is carried out until that relative motion comes to a standstill, and a subsequent acceleration in an opposite direction of the scan line is carried out until the scanning speed is reached, and the control device performs a superimposition on that relative motion with regard to acceleration and subsequent deceleration of a relative motion between camera and wafer perpendicular to the scan lines until the new scan line is reached.

In a further embodiment of the invention the object is achieved, with an apparatus comprising: a camera for on-the-fly acquisition of images with an image field of a plurality of regions on the wafer, a plurality of scan lines are defined and the wafer is divided into that plurality of scan lines, means for scanning the wafer with a scanning speed in a scan line direction as a relative motion between the camera and the wafer, the image field of the camera has a rectangular configuration, and a short side of the rectangular configuration of the image field is oriented parallel to the scan line direction.

According to the present invention, upon a scan line change the relative motions between wafer and camera, in the scan line direction and perpendicular to the scan line direction, occur in such a way that they are at least partially superimposed. As a result of this superimposition of the relative motions, a continuously curved displacement track is described. "Continuously curved" is to be understood to mean that an abrupt change in direction, which would cause an inflection in the displacement track, does not take place. In the case of a conventional displacement track, on the other hand, the displacement tracks are perpendicular to one another, and the relative motions are performed one after another. As a result of these separate relative motions—only parallel or only perpendicular to the scan lines—the conventional displacement track is not continuously curved (in the aforementioned sense) in the context of the abrupt 90-degree change in displacement direction.

There are various possibilities for embodying the superimposition according to the present invention of the relative motions parallel and perpendicular to the scan lines. In general, the parallel and perpendicular acceleration motions can begin at different points in time and also be completed at different points in time. In other words, the deceleration in the scan line direction can initially begin before the acceleration perpendicular to the scan lines is accomplished, or vice versa. This depends on whether the adjacent scan line, or one farther away, is to be scanned next. The acceleration phases for the two motion directions can correspondingly also be completed at different times. The motions in the two directions can thus be phase-shifted and can have different durations. This also implies different accelerations and different forces on the moving parts.

The advantage of the superimposed motions is that the time for a scan line changeover is shortened. In the time frame in which the motion direction parallel to the scan lines is reversed, the motion perpendicular to the scan lines is accomplished (or vice versa). As a result of these motions parallel and perpendicular to the scan lines that occur simultaneously at least in a time interval within the time frame, the time needed to reach the next line to be scanned is decreased. The throughput rate of wafers to be examined is thus increased.

In one possible embodiment, the decelerating and accelerating relative motions in the scan line direction and perpendicular thereto begin, at the earliest, after imaging of a last region of the current scan line that is to be imaged. In addition, the scanning speed in the opposite scan line direction should be reached, and the relative speed perpendicular to the scan lines should go to zero, at the latest upon reaching a region that is to be imaged next.

In an embodiment of the invention specific to this, the deceleration parallel to the scan lines and the acceleration perpendicular to the scan lines begin simultaneously, and the acceleration parallel to the scan lines and the deceleration perpendicular to the scan lines are completed simultaneously. Additional time is saved if the beginning of these motion operations occurs immediately after acquisition of the last image to be acquired in the scan line, or if these motion operations are completed just as the next image to be acquired in the new scan line is reached. As a result, the motion operations upon scan line changeover are optimized even in a context of scan lines of different lengths.

In another possible embodiment, the deceleration in the scan line direction begins even before imaging of a region that is the last to be imaged in the current scan line. As a result the last region, or even several of the last regions, to be imaged in the current scan line are acquired by the camera at a scanning speed that is reduced in accordance with the deceleration. This deceleration operation that is initiated even before the last image acquisition yields time advantages especially at high scanning speeds. A relative motion perpendicular to the scan lines of course does not occur until the last image acquisition.

Similarly, the scanning speed in the opposite scan line direction can also be reached only after a region to be imaged next in the new scan line is reached. This means that the first image or images to be acquired are not yet acquired at the full scanning speed, so that time advantages also result therefrom because of the shortened scan line changeover. In order to obtain a complete image, the relative motion perpendicular to the scan lines must of course be completed no later than the first image acquisition in the new scan line.

A further special case exists when the greatest relative speed perpendicular to the scan lines is reached upon reaching a relative speed of zero in the scan line direction. This is advantageous principally with scan lines of identical or at least similar length, since the deceleration and acceleration forces during the scan line changeover are uniformly distributed. In addition, constant acceleration values for both motion directions can also be used in this context.

The acceleration values upon deceleration and acceleration in and perpendicular to the scan line direction can also, however, be modified continuously so that the resulting forces change continuously. This means particularly smooth starting and stopping.

The relative motions between wafer and camera can be implemented in various ways. On the one hand, the camera can be guided in both motion directions over a fixed wafer, and can thereby reach every point on the wafer. On the other hand, the wafer can be placed on an X/Y scanning stage that is displaced beneath a stationary camera. In many cases an X/Y scanning stage and a fixed camera are used.

Combinations thereof are of course also possible; i.e. a scanning stage moves exclusively in one of the two motion directions while the camera is moved only in the direction perpendicular thereto. The advantage of this kind of combination is either that a scanning stage movable in only one dimension is needed or that, in the case of an X/Y scanning stage, that direction in which only the upper part of the scanning stage is displaced can be preferred. In both cases, a greater acceleration can be attained because of the smaller moving mass, or the drive unit of the stage can be designed for smaller loads. Decreased wear and a longer service life also result.

The invention yields the time advantages just described for all types of scans. The time advantages are perceptible both when scanning individual selected scan lines, in which context regions on the wafer adjacent to one another in the scan line direction are imaged with the camera, and in the case of wafers to be scanned completely for imaging of the entire wafer surface. But the aforementioned method with the initiation of motion changes directly after the last image acquisition is also advantageous for camera imaging of random-sample imaging of individual regions scattered over the wafer, since in this context it is also not necessary to travel over complete scan lines. In this case the relative motion is also performed obliquely with reference to the scan lines.

A further time saving results from the fact that in the context of a rectangularly configured camera image field, the short side of the image field rectangle is oriented parallel to the scan line direction, in contrast to the hitherto usual arrangement with the longer image field side parallel to the scan lines. There is of course no change in the total area to be scanned as a result of rotating the camera 90 degrees about its imaging axis, but the longer image field side now determines the width of a scan line, thereby decreasing the number of scan lines required. Fewer scan line changeovers are therefore needed in order to scan a wafer, and corresponding time reductions result. The time savings become especially perceptible when many scan lines need to be scanned.

A scan line is normally traversed at the maximum possible speed. Since a sufficiently high illumination density for on-the-fly images usually cannot be achieved with continuous illumination over the entire wafer, flash units are used. In addition, the light is concentrated only onto the region being imaged. The maximum scan speed is limited by the maximum flash rate of the flash units at a corresponding illumination intensity, and by the frame rate of the camera or the frame grabber electronics. When a short rectangle side of the camera image field is oriented parallel to the scan lines, the maximum displacement speed will therefore be lower in order to have the same required image acquisition time. A lower speed in the scan line direction, however, also means a shorter reversal time for the motion in the opposite scan line direction, since it is only a lower speed that needs to be decelerated and accelerated again.

The displacement path perpendicular to the scan lines to an adjacent scan line becomes greater, however, since the longer edge of the camera image field rectangle now determines the width of the scan lines. The acceleration perpendicular to the scan lines must therefore be increased if, in the optimum case, identical times are to be achieved for the parallel and perpendicular acceleration motions upon scan line changeover.

The total time for the motion between the end point of the one line and the starting point of the next—the line changeover time $t_{zw}$—is defined, assuming constant accelerations $\alpha_x$ in the scan line direction and $\alpha_y$ perpendicular to the scan line direction, as:

$$t_{zw} = t_{\Delta x} + t_x = t_y = \frac{\Delta x}{v_{max}} + 2 * \frac{v_{max}}{a_x} = 2 * \sqrt{\frac{\Delta y}{a_y}}$$

where $t_x$ is the time for deceleration and acceleration in the scan line direction and $t_y$ the time for the motion perpendicular to the scan line direction, $v_{max}$ is the scanning speed, $\Delta x$ is the difference between the starting and ending points of the two scan lines in the scan line direction and $t_{\Delta x}$ the corresponding time, and $\Delta y$ is the spacing between two scan lines perpendicular to the scan line direction.

The required constant acceleration perpendicular to the scan line direction can be calculated, assuming scan lines of identical length ($\Delta x=0$), as:

$$a_y = \frac{a_x^2 * \Delta y}{v_{max}^2}.$$

Depending on the feature sizes to be imaged on the wafer, the invention can be carried out using a camera without additional optics, or the camera can be mounted on a macroscope or a microscope in order to acquire correspondingly magnified images. Defects on the features or the interstices can be ascertained in this context, or measurements of the features can be performed.

BRIEF DESCRIPTION OF THE DRAWINGS

The invention will be explained in more detail below with reference to the exemplary embodiments depicted in the schematic drawings, in which.

DETAILED DESCRIPTION OF THE INVENTION

Figure 1:
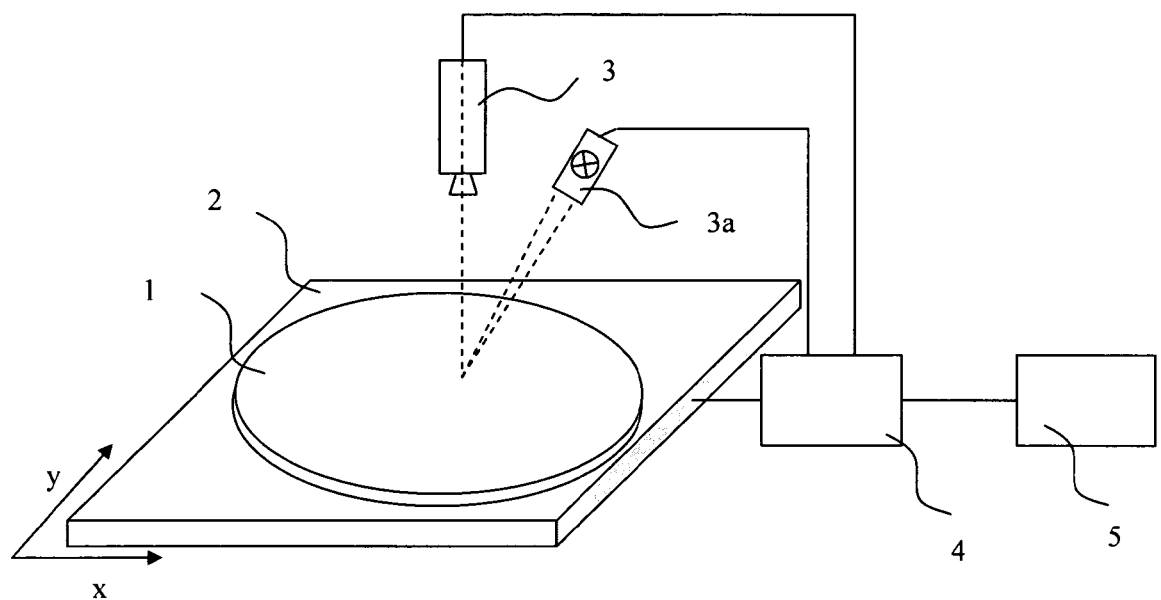
FIG. 1 shows an arrangement of a camera, stage with wafer, and control device.

FIG. 1 schematically shows a wafer 1 to be scanned, which is located on a scanning stage 2 and of which a plurality of images are acquired by means of a camera 3. In the exemplary embodiment of FIG. 2, an X/Y scanning stage that can be displaced in the X and Y coordinate directions is used to produce a relative motion between scanning stage 2 and camera 3. Camera 3 is installed immovably with respect to scanning stage 2.

To allow a large number of image acquisitions to be performed with camera 3 in a short time, scanning stage 2 is displaced beneath camera 3 at a constant speed without stopping. The desired images, of selected regions or of the entire surface of wafer 1, are thus acquired on the fly. A control unit 4 determines the motion and speed of scanning stage 2, and also controls camera 3. This coordinated control of scanning stage 2 and camera 3 makes possible imaging of the desired regions of wafer 1.

The on-the-fly image acquisitions necessitate, as a function of the speed of scanning stage 2, correspondingly short exposure times for the individual images so that blurred images are prevented. Short exposure times mean that the wafer must be illuminated with a very high light intensity. A high illumination density can be achieved by the fact that an illumination device 3a concentrates the light that it generates only onto an area of wafer 1 that is necessary for acquisition of an image using camera 3.

The light of illumination device 3a can additionally be pulsed in order to generate an even greater light intensity. This can be achieved with a commercially available flash lamp that emits its light only for the brief image acquisition time. The flash lamp is triggered, as a function of the position of scanning stage 2, in such a way that the desired regions of wafer 1 are imaged. If a scan line is to be completely imaged from one edge of the wafer to the opposite edge, the flash frequency of the flash lamp and the speed of scanning stage 2 are coordinated with one another in such a way that the exposed regions, and thus the acquired images, are at least directly adjacent to one another. The usual practice is to work with an overlap of the imaged regions to ensure that no image information on the scan line is lost. The overlapping regions are taken into account by an image processing system.

The acquired images are evaluated directly after they are acquired, using a fast-executing algorithm. They can also, of course, be first stored and evaluated later.

When a flash lamp is used, camera 3 can also be operated without a mechanical or electronic shutter, since the exposure time is defined by the duration of the light flash. The electronic light sensor of the camera—usually a two-dimensional CCD array or a one-dimensional linear sensor—is read out after the exposures. A corresponding control system can be provided in camera 3, or camera 3, illumination device 3a, and the scanning stage can be controlled entirely by control unit 4. As an alternative, scanning stage 2 can also generate trigger signals in accordance with its position in the X/Y coordinate system, and can activate illumination device 3a and camera 3 via control unit 4. Control unit 4 is generally connected to a computer 5 that monitors control unit 4 via software and receives the acquired images from camera 3. The computer can also store and evaluate the images.

As modified exemplary embodiments of the relative motion between scanning stage 2 and camera 3 described above, an arrangement having a stationary stage 2 and a camera 3 movable in the X and Y directions, optionally together with illumination device 3a, can also be used instead of an X/Y scanning stage 2. A combination of a displaceable (e.g. only in the X direction) stage and a displaceable (e.g. only in the Y direction) camera 2 is also possible.

Figure 2:
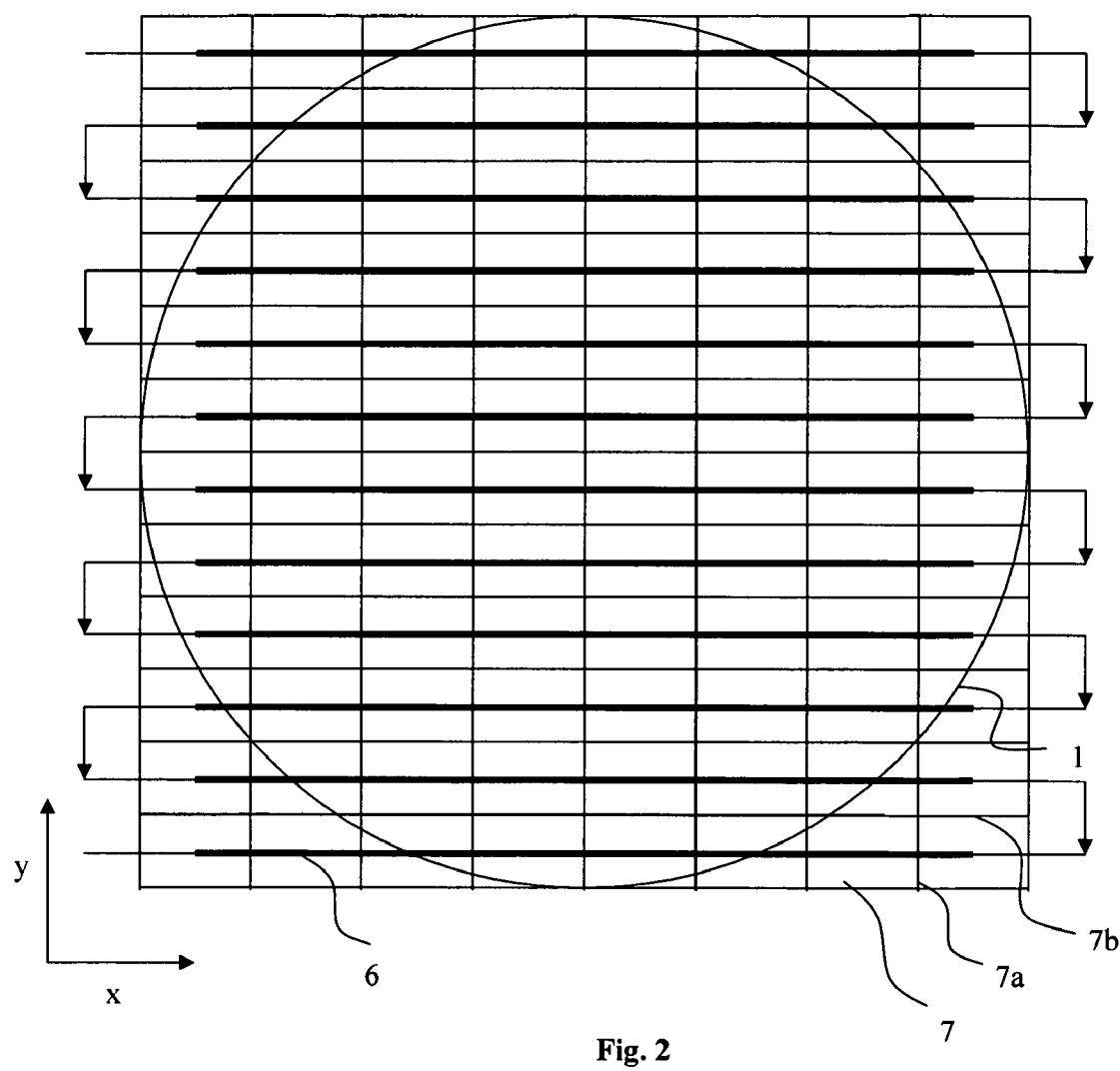
FIG. 2 shows a conventional scanning track (existing art)

FIG. 2 depicts a conventional scan track 6 for a scanning routine in which wafer 1 is completely scanned. Images of the entire wafer surface are acquired for 100% inspection. Wafer 1 is scanned line-by-line in such a way that rectangle sides 7a, 7b of adjacent image areas, which each correspond to image field 7 of camera 3, are at least adjacent to one another. The scan lines possess a uniform length and cover the wafer at its diameter. The scan lines thus each begin and end at a specific X coordinate outside the wafer.

Scanning stage 2 is stopped at the end of a scan line. Its speed at this point in the X direction (and in the Y direction) is therefore zero. It then accelerates in the Y direction perpendicular to the scan line, travels as far as the adjacent scan line, and there once again comes to a standstill. It is then moved in the opposite scan line direction, i.e. at an opposite speed compared with the previous scan line. This operation repeats at every scan line changeover. The overall result of this is a scan track proceeding in rectangular fashion.

Figure 3:
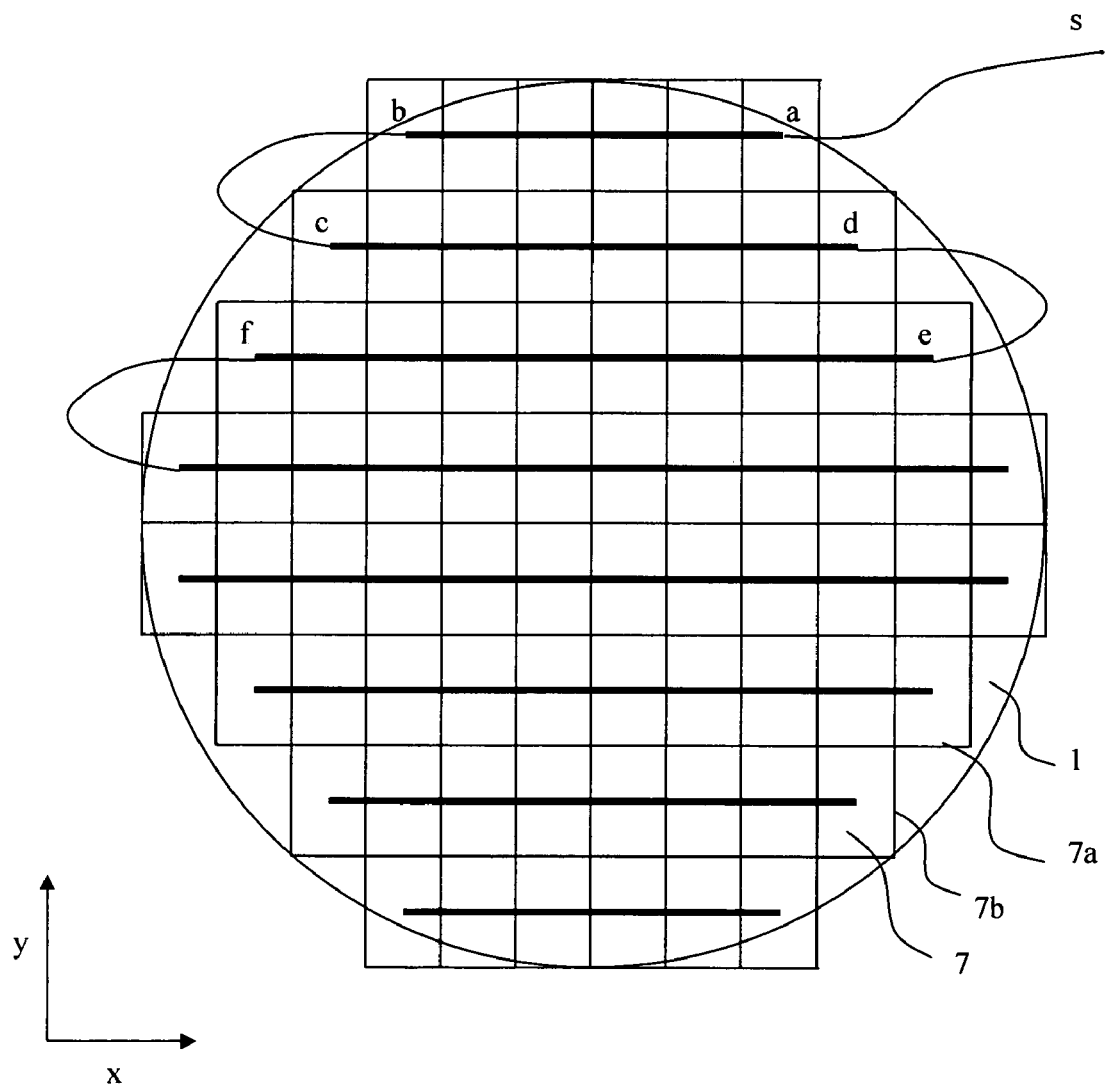
FIG. 3 shows a scanning track according to the present invention.

In contrast to this, the profile shown in FIG. 3 of scanning track s according to the present invention is continuously curved at each scan line changeover. In this exemplary embodiment, scanning stage 2 is displaced simultaneously in the X and Y directions during a scan line changeover. While scanning stage 2 is being decelerated in the X direction (which corresponds to the scan line direction), an acceleration in the Y direction (perpendicular to the scan lines) is simultaneously being accomplished. Scanning stage 2 is accelerated in the opposite X direction and decelerated again in the Y direction, so that the intended scanning speed is reached at the first image acquisition location in the next scan line to be scanned. Wafer 1 is thus scanned in meander fashion.

As a result of the simultaneous movement of scanning stage 2 in both the X and Y directions, time is saved upon changeover of the scan lines as compared with the example of FIG. 2. The length of the adjacent scan line, or the next scan line to be scanned, can furthermore be taken into account. If that line is shorter or longer than the scan line just scanned, additional time can be saved if the reversal points are adapted to correspond to the ends of the scan lines and are not always located at the same X coordinate, as is the case in FIG. 2.

FIG. 3 thus indicates how, after a first short scan line has been scanned from scan line ends a to b, a changeover in scan lines is accomplished from end b to end c of a longer scan line. The shape of this scan track, with associated differing acceleration values for scanning stage 2 in both the X and Y direction, is somewhat different than in the case of the scan line changeover from ends d to e. The meander-shaped scan is thus advantageously adapted to the scan line lengths—or, if the entire wafer surface is being examined, to the shape of wafer 1.

It is of course advantageous in terms of time if the corresponding X and Y accelerations for the scan line changeover begin immediately after the last image acquisition in a scan line. This need not always necessarily be the case, however. Depending on the scan speed and the distance to the next point to be traveled to, the accelerations in the Y direction can begin at a later point in time than the accelerations in the X direction, and vice versa. The same is true, analogously, of the end of the accelerations in the X and Y directions. The forces on the bearings, of the scanning stage can thus be adjusted so as to achieve less wear and a longer service life for scanning stage 2, with an optimum time for the scan line changeover.

It is additionally evident from FIG. 3 that image field 7 of camera 3 is oriented with the shorter rectangle side parallel (and longer rectangle side 7b therefore perpendicular) to the scan lines, in contrast to the conventional orientation of the image field shown in FIG. 2. The number of scan lines for an area to be scanned on wafer 1 can thereby be decreased. Since fewer scan line changeovers are necessary as a result, the overall scanning time is reduced by an amount equal to the time not needed for those line changeovers. This is an additional time saving. The speed of scanning stage 2 is decreased in this context so that the exposure time for each image field remains unchanged.

In summary, the throughput of wafers 1 is considerably increased as a result of the time saved by superimposing the accelerations and motions in the X and Y directions upon scan line changeover. The throughput can be additionally increased by reducing the number of scan lines needed, by orienting shorter side 7a parallel to the scan lines. The effects become that much more perceptible as the number of scan lines increases, i.e. in particular for a complete scan of wafer 1.

What is claimed is:

1. A method for scanning a semiconductor wafer, comprising the steps of:
    creating a relative motion between a camera and the wafer to scan the wafer along a plurality of scan lines;
    acquiring images of regions on the wafer with the camera at a scanning speed along a direction of a current scan line,
    changing the direction of scanning from the current scan line to an opposite scan line that is to be scanned next, by:
        decelerating the relative motion in the direction of scanning along the current scan line until that relative motion comes to a standstill, and
        accelerating the relative motion in the direction of scanning along the opposite scan line until the scanning speed is reached, and
    superimposing at least partially the steps of accelerating and decelerating the relative motion between the camera and wafer the until the opposite scan line is reached.

2. The method as defined in claim 1, further comprising:
    starting decelerating and accelerating of the relative motion in the scan line direction and a perpendicular direction thereto after imaging of a last region of the current scan line; and reaching the scanning speed along the opposite scan line direction and zeroing a relative speed in the perpendicular direction at the latest upon reaching a region that is to be imaged next.

3. The method as defined in claim 1, further comprising:
starting decelerating and accelerating of the relative motion in the scan line direction and a perpendicular direction thereto after imaging of a last region of the current scan line; or
reaching the scanning speed along the opposite scan line direction and zeroing a relative speed in the perpendicular direction at the latest upon reaching a region that is to be imaged next.

4. The method as defined in claim 1, wherein decelerating in the direction of scanning and accelerating in the direction perpendicular to scan lines begin simultaneously, and wherein accelerating in the direction of scanning decelerating in the direction perpendicular to the direction of scanning are completed simultaneously.

5. The method as defined in claim 1, wherein decelerating in the direction of scanning begins before imaging of a region that is the last to be imaged in the current scan line.

6. The method as defined in claim 1, wherein the scanning speed in the opposite scan line direction is reached after a region to be imaged next in the opposite scan line is reached.

7. The method as defined in claim 1, further comprising reaching a highest relative speed perpendicular to the scan lines when a relative speed of zero in the direction of scanning is reached.

8. The method as defined in claim 1, further comprising continuously modifying acceleration values during deceleration and acceleration in the direction of scanning along the current scan line and a direction perpendicular to the scan line.

9. The method as defined in claim 1, wherein regions on the wafer adjacent to one another in the scan line direction are imaged with the camera.

10. The method as defined in claim 9, wherein regions adjacent to one another on the wafer are imaged in such a way that their images partially overlap.

11. The method as defined in claim 1, wherein the wafer is completely scanned, and images of the entire surface of the wafer are acquired.

12. The method as defined in claim 11, wherein regions adjacent to one another on the wafer are imaged in such a way that their images partially overlap.

13. The method as defined in claim 1, wherein the camera defines a rectangularly configured image field having a short side oriented parallel to the scan line direction.

14. An apparatus for scanning a semiconductor wafer along a plurality of scan lines comprising:
a camera for on-the-fly acquisition of images of a plurality of regions on the wafer disposed on a scanning stage,
means for generating a relative motion between the camera and the wafer thereby defining a scanning speed in a direction of the scan line,
a control device for decelerating the relative motion in the direction of the scan line during a changeover from a current scan line to a new scan line until that relative motion comes to a standstill, and a subsequent acceleration in an opposite direction of the scan line is carried out until the scanning speed is reached, the control device being coupled to the scanning stage and to the camera serving to perform a superimposition of accelerating and decelerating of the relative motion between the camera and the wafer until the new scan line is reached.

15. The apparatus as defined in claim 14, wherein in the camera defines a rectangularly configured image field having a short side oriented parallel to the scan line direction.

16. The apparatus as defined in claim 14, wherein the camera is stationary and the scanning stage performs the relative motion relative the camera.

17. An apparatus for scanning a semiconductor wafer comprising:
a camera for on-the-fly acquisition of images with an image field of a plurality of regions on the wafer, the wafer being divided into a plurality of defined scan lines;
means for scanning the wafer with a scanning speed in a scan line direction during relative motion between the camera and the wafer, the image field of the camera having a rectangular configuration, with a short side of the rectangular configuration of the image field being oriented parallel to the scan line direction.

* * * * *